(12) United States Patent
Elrod (10) Patent No.: US 12,372,507 B2
(45) Date of Patent: Jul. 29, 2025

(54) INPUT CONTROL BASED ON ATMOSPHERIC OXYGEN

(71) Applicant: Scott A. Elrod, Lake Jackson, TX (US)

(72) Inventor: Scott A. Elrod, Lake Jackson, TX (US)

(*) Notice: Subject to any disclaimer, the term of this patent is extended or adjusted under 35 U.S.C. 154(b) by 43 days.

(21) Appl. No.: 18/146,559

(22) Filed: Dec. 27, 2022

(65) Prior Publication Data

US 2024/0210370 A1 Jun. 27, 2024

(51) Int. Cl.
*F02D 41/14* (2006.01)
*G01N 33/00* (2006.01)

(52) U.S. Cl.
CPC ..... *G01N 33/0036* (2013.01); *F02D 41/1454* (2013.01); *G01N 33/0068* (2024.05)

(58) Field of Classification Search
CPC ...... B60H 1/008; B60H 3/0007; B60K 35/00; G01S 19/13; G01N 33/00; G01N 33/0036; F02D 41/14; F02D 41/1454
See application file for complete search history.

(56) References Cited

U.S. PATENT DOCUMENTS

| | | | | |
|---|---|---|---|---|
| 4,601,809 A * | 7/1986 | Kitahara | ............ | G01N 27/4065 123/693 |
| 6,471,840 B1 * | 10/2002 | Gao | ................ | G01N 27/4175 204/426 |
| 6,805,782 B2 * | 10/2004 | Tanaka | ................. | G01N 27/419 204/427 |
| 2002/0152009 A1 * | 10/2002 | Bartoli | .................... | G01L 3/24 340/439 |
| 2012/0097050 A1 * | 4/2012 | Schaefer | ................ | A23B 7/144 99/468 |
| 2012/0325662 A1 * | 12/2012 | Inagaki | ................ | G01N 27/409 204/435 |
| 2013/0112157 A1 * | 5/2013 | Brown | ................... | F02M 25/12 123/3 |
| 2014/0242225 A1 * | 8/2014 | Schaefer | ................ | A23B 7/148 99/468 |
| 2014/0318989 A1 * | 10/2014 | Dhas | .................... | B60H 3/0007 205/785.5 |
| 2014/0326021 A1 * | 11/2014 | Wagner | ................ | B01D 53/047 62/617 |
| 2016/0102619 A1 | 4/2016 | Hakeem et al. | | |
| 2016/0115883 A1 | 4/2016 | Mischler et al. | | |
| 2016/0363551 A1 * | 12/2016 | Morishita | .............. | G01N 27/04 |
| 2017/0204814 A1 * | 7/2017 | Yokono | ............... | F02D 41/1454 |
| 2017/0370013 A1 | 12/2017 | Bahar et al. | | |

(Continued)

OTHER PUBLICATIONS

PCT/US2023/085598 International Search Report and Written Opinion dated Apr. 11, 2024 (14 pages).

*Primary Examiner* — Hai H Huynh
*Assistant Examiner* — Johnny H Hoang
(74) *Attorney, Agent, or Firm* — DORSEY & WHITNEY LLP (57) ABSTRACT

An exemplary method adjusts one or operating characteristics of an oxygen utilizing system based on atmospheric oxygen content. The method includes detecting, using one or more atmospheric sensors, atmospheric conditions for an atmosphere surrounding the oxygen utilizing system and determining the atmospheric oxygen content based on the detected atmospheric conditions. The method further includes adjusting the one or more operating characteristics of the oxygen utilizing system based on the atmospheric oxygen content.

17 Claims, 7 Drawing Sheets

(56) References Cited

U.S. PATENT DOCUMENTS

| | | |
|---|---|---|
| 2019/0106132 A1 | 4/2019 | Lavertu et al. |
| 2019/0160907 A1* | 5/2019 | Velazquez ............. B60H 1/248 |
| 2020/0116090 A1 | 4/2020 | Van Tran et al. |
| 2021/0054796 A1* | 2/2021 | Okamoto ............ F02D 41/1475 |

* cited by examiner

FIG. 5 ized in that:
INPUT CONTROL BASED ON ATMOSPHERIC OXYGEN

TECHNICAL FIELD

This application relates to methods and systems for adjusting engine characteristics based on atmospheric oxygen content.

BACKGROUND

Various systems utilize atmospheric oxygen to perform a variety of functions. For example, ozone generators, such as those used for water treatment or indoor air purification, utilize atmospheric oxygen to produce ozone. Engine performance in motorized vehicles (e.g., automobiles, trucks, trains, aircraft, and the like) and other oxygen utilizing appliances is also affected by the amount of atmospheric oxygen available for use by the engine. The amount of atmospheric oxygen available for use by such oxygen utilizing systems may vary based on environmental factors, such as altitude, temperature, and humidity.

SUMMARY

An exemplary method disclosed herein adjusts one or operating characteristics of an oxygen utilizing system based on atmospheric oxygen content. The method includes detecting, using one or more atmospheric sensors, atmospheric conditions for an atmosphere surrounding the oxygen utilizing system and determining the atmospheric oxygen content based on the detected atmospheric conditions. The method further includes adjusting the one or more operating characteristics of the oxygen utilizing system based on the atmospheric oxygen content.

An example system disclosed herein includes one or more atmospheric sensors configured to detect atmospheric conditions of an atmosphere surrounding an oxygen utilizing system. A sensor computer in communication with the one or more atmospheric sensors is configured to determine an atmospheric oxygen content based on the detected atmospheric conditions received from the one or more atmospheric sensors. A control system of the oxygen utilizing system in communication with the sensor computer is configured to adjust one or more operating characteristics of the oxygen utilizing system based on the atmospheric oxygen content received from the sensor computer.

Example non-transitory computer readable media are encoded with instructions which, when executed by one or more processors, cause the one or more processors to receive, from one or more atmospheric sensors, atmospheric conditions for an atmosphere surrounding an oxygen utilizing system; determine an atmospheric oxygen content based on the received atmospheric condition; and adjust one or more operating characteristics of the oxygen utilizing system based on the atmospheric oxygen content.

Additional embodiments and features are set forth in part in the description that follows, and will become apparent to those skilled in the art upon examination of the specification and may be learned by the practice of the disclosed subject matter. A further understanding of the nature and advantages of the present disclosure may be realized by reference to the remaining portions of the specification and the drawings, which form a part of this disclosure. One of skill in the art will understand that each of the various aspects and features of the disclosure may advantageously be used separately in some instances, or in combination with other aspects and features of the disclosure in other instances.

BRIEF DESCRIPTION OF THE DRAWINGS

The description will be more fully understood with reference to the following figures in which components are not drawn to scale, which are presented as various examples of the present disclosure and should not be construed as a complete recitation of the scope of the disclosure, characterized in that.

DETAILED DESCRIPTION

Methods and systems described herein may utilize atmospheric sensors to detect various atmospheric conditions (e.g., altitude, temperature, air pressure, and the like), which may be used to determine atmospheric oxygen content. Atmospheric oxygen content may be used to adjust operations of various oxygen utilizing systems, such as various types of engines, ozone generators, and other systems that may monitor and/or vary the amount of oxygen needed to be produced or maintained. For example, engine operation characteristics (such as the amount of fuel provided to the engine) may be adjusted to accommodate for the atmospheric oxygen content to preserve the performance of the engine. Such methods and systems may be useful in remote locations without connectivity to WiFi, global positioning satellite (GPS) networks, and/or other networks which may provide data on location of an oxygen utilizing system. The methods and systems may further be useful for engines or other systems which may rely on oxygen sensors to adjust system characteristics, as such oxygen sensors may fail, leading to decreased system performance as system inputs may not be adjusted based on atmospheric oxygen content.

Figure 1:
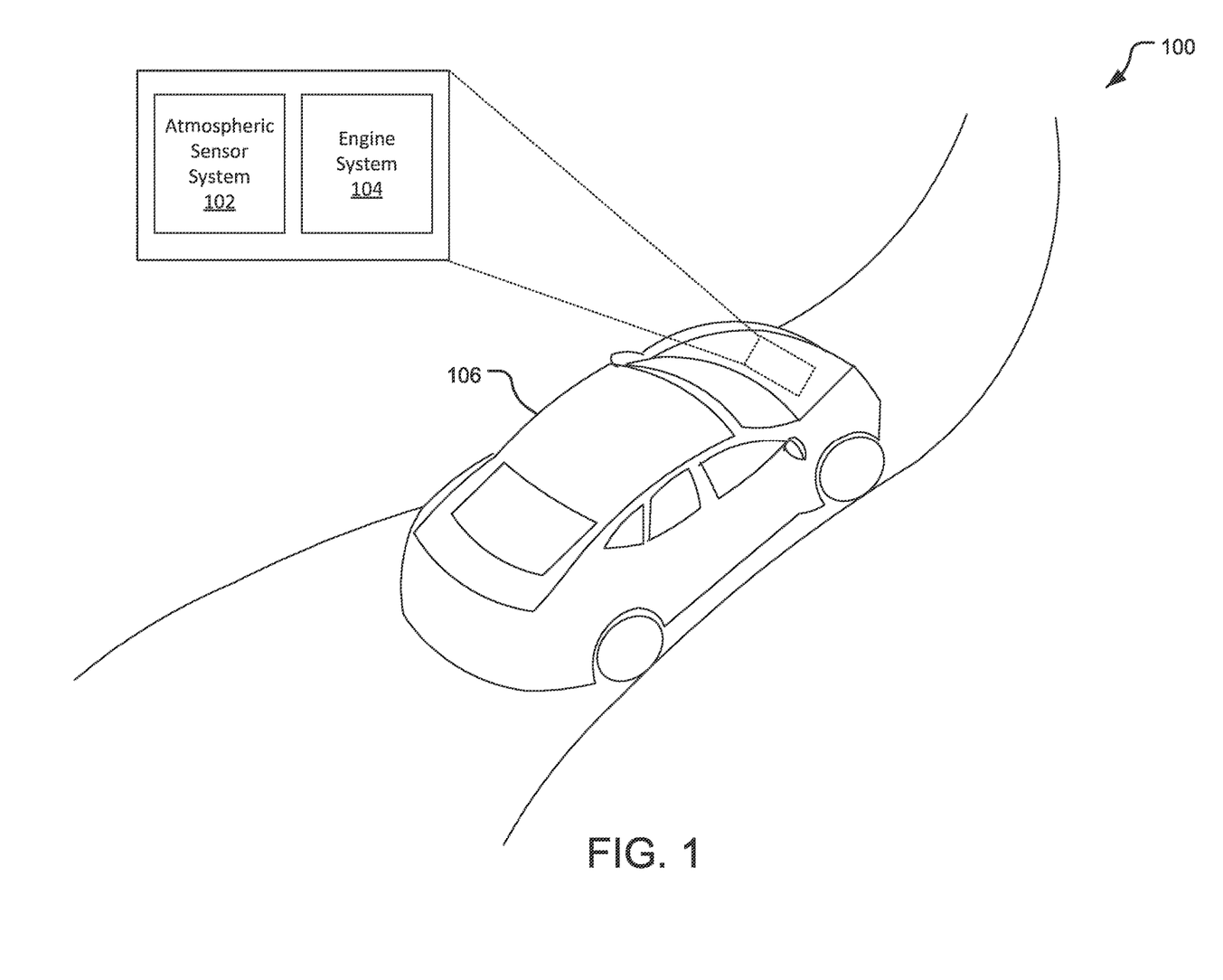
FIG. 1 illustrates an example environment for use of an atmospheric sensor system and an engine system, in accordance with various embodiments of the disclosure.

Various embodiments of the present disclosure will be explained below in detail with reference to the accompanying drawings. Other embodiments may be utilized, and structural, logical and electrical changes may be made without departing from the scope of the present disclosure. FIG. 1 illustrates an example environment 100 for use of an atmospheric sensor system 102 and an engine system 104. The environment 100 is exemplary and the atmospheric sensor system 102 may be used in other environments and with other oxygen utilizing systems as described herein. As shown in FIG. 1, the atmospheric sensor system 102 may be used in conjunction with an engine system 104 in an automobile 106. Though the atmospheric sensor system 102 is shown being used in conjunction with an automobile 106, the atmospheric sensor system 102 may be used in conjunction with various types of engines in various applications. For example, an atmospheric sensor system 102 may be used for engines powering automobiles, off-road vehicles, trains, boats, aircraft, landscaping equipment, electrical generators, construction equipment, and the like. The atmospheric sensor system 102 may be used in conjunction with gas engines (e.g., internal combustion engines running on gaseous fuel), diesel engines, or other types of engines.

The atmospheric sensor system 102 may, in some examples, be used without input from conventional oxygen sensors placed, for example, at outlets of engines. Accordingly, the atmospheric sensor system 102 may provide redundancy for situations where oxygen sensors may be difficult to replace, such as when using various equipment (e.g., vehicles, generators, and the like) in remote locations. Further, the atmospheric sensor system 102 may be used without connectivity to additional information which may be available, for example, through GPS networks, cellular data networks, and/or other wireless networks. Accordingly, the atmospheric sensor system 102 may be useful for preserving engine performance in remote locations where such data is not readily available. The atmospheric sensor system 102 may further adjust engine performance using real-time data from the atmospheric sensor system 102 instead of from data obtained from a remote location, which may be less accurate. For example, such remote data may be time delayed or may reflect conditions at an approximate location, rather than an exact location. For example, GPS location may be inaccurate. In areas with dramatic elevation changes (e.g., in mountain environments), such inaccuracies in location may result in incorrect estimates of altitude, negatively affecting engine performance.

In various examples, one or more components of the atmospheric sensor system 102 may be placed near to, remote from, and/or be integrated into the engine system 104. For example, sensors of the atmospheric sensor system 102 may be mounted to an exterior of a vehicle, while the sensor computer 110 may be located locally to the engine system 104. In some examples, the sensor computer 110 may share processing and/or memory resources with an engine control system of the engine system 104.

In various examples, the atmospheric sensor system 102 may communicate with the engine system 104 through a wired connection, such as a universal serial bus (USB), Ethernet, twisted pair, or other types of wired connections. In some examples, the atmospheric sensor system 102 may communicate with the engine system 104 using wireless communication protocols, such as a Bluetooth connection. Generally, the atmospheric sensor system 102 may communicate calculated or approximate atmospheric oxygen levels, and the engine system 104 may adjust engine operation characteristics to preserve engine performance in various environments with varying atmospheric oxygen levels.

The environment 100 may include additional components not shown in FIG. 1, which components may be in communication with, or used by, the atmospheric sensor system 102. For example, the atmospheric sensor system may communicate with mobile devices (such as smart phones, tablets, smart watches, and the like), equipment (e.g., the automobile 106), and the like. Such devices may be used to provide information or commands to the atmospheric sensor system 102. For example, a user may request that the atmospheric sensor system 102 collect sensor data to determine atmospheric oxygen content and adjust engine operation accordingly. Such functionality may be used, for example, to adjust engine performance when, for example, a generator is set up in a new location. In some examples, the atmospheric sensor system 102 may further utilize sensors of mobile devices in communication with the atmospheric sensor system 102. For example, the atmospheric sensor system 102 may utilize altimeters in mobile devices to monitor functionality of altimeters in the atmospheric sensor system 102 and/or to provide additional data points. Similarly, the atmospheric sensor system 102 may utilize sensors included, for example, in an automobile to provide additional data to calculate atmospheric oxygen content. For example, the atmospheric sensor system 102 may utilize a thermometer of an automobile to receive atmospheric temperature data used to calculate atmospheric oxygen content.

Such devices may further be used to display information generated by the atmospheric sensor system 102. For example, the atmospheric sensor system may communicate with a mobile device to display a notification when a change in atmospheric conditions (e.g., a change in altitude) is detected and/or when a malfunction of a sensor in the atmospheric sensor system 102 is detected. In various examples, the atmospheric sensor system may provide or connect with a mobile application at such mobile devices, which may display other information about the atmospheric sensor system 102, such as power status, readings from sensors of the atmospheric sensor system 102, engine performance, and the like. In some examples, similar information may be displayed, for example, using systems within an interior of a vehicle, such as an infotainment system within a passenger car.

The atmospheric sensor system 102 may further communicate with additional external data sources, such as GPS networks, cloud computing locations, and the like, when available and within range of the atmospheric sensor system 102. Though the atmospheric sensor system 102 may function without data from such sources, the atmospheric sensor system 102 may, in various examples, use such data to detect malfunction of sensors, calibrate sensors, and/or to provide additional data points for calculation of atmospheric oxygen content.

Though FIG. 1 is shown with reference to an engine of an automobile, the atmospheric sensor system 102 may, in various examples, be used with other types of oxygen utilizing systems. For example, the atmospheric sensor system 102 may be used with oxidant output sources, such as ozone generators, which may operate using atmospheric oxygen. Such systems may be used, for example, for water purification or other applications which may similarly be conducted out of range of GPS or other data sources used to calculate expected atmospheric oxygen concentration. Accordingly, the atmospheric sensor system 102 may provide data on atmospheric oxygen levels, such that operating characteristics of such oxidant output sources may be adjusted to compensate for changes in atmospheric oxygen levels. For example, an ozone generator may utilize ambient air to create ozone, and may use a fan or other method as intake for the ambient air. Where there is a lower concentration of atmospheric oxygen, the fan or other intake may be adjusted to intake more ambient air, which may keep the production of ozone consistent where atmospheric oxygen content changes.

In various examples, such ozone generators may be utilized to, for example, treat water or as part of systems used to generate water, in conjunction with other components. For example, ozone created by an ozone generator may be combined with hydrocarbons to generate water. In another example, ozone created by an ozone generator may be used to treat water removed from atmospheric air through a dehumidifier or other system.

In other examples, the atmospheric sensor system 102 may be used in conjunction with systems which utilize condensed or liquid oxygen. For example, some systems may utilize liquid or condensed oxygen and may generate such liquid or condensed oxygen utilizing oxygen from ambient air. Such systems may use a fan or other method as intake for ambient air. Where there is a lower concentration of atmospheric oxygen, the fan or other intake may be adjusted to intake more ambient air, which may keep the production of ozone consistent where atmospheric oxygen content changes.

Figure 2A:
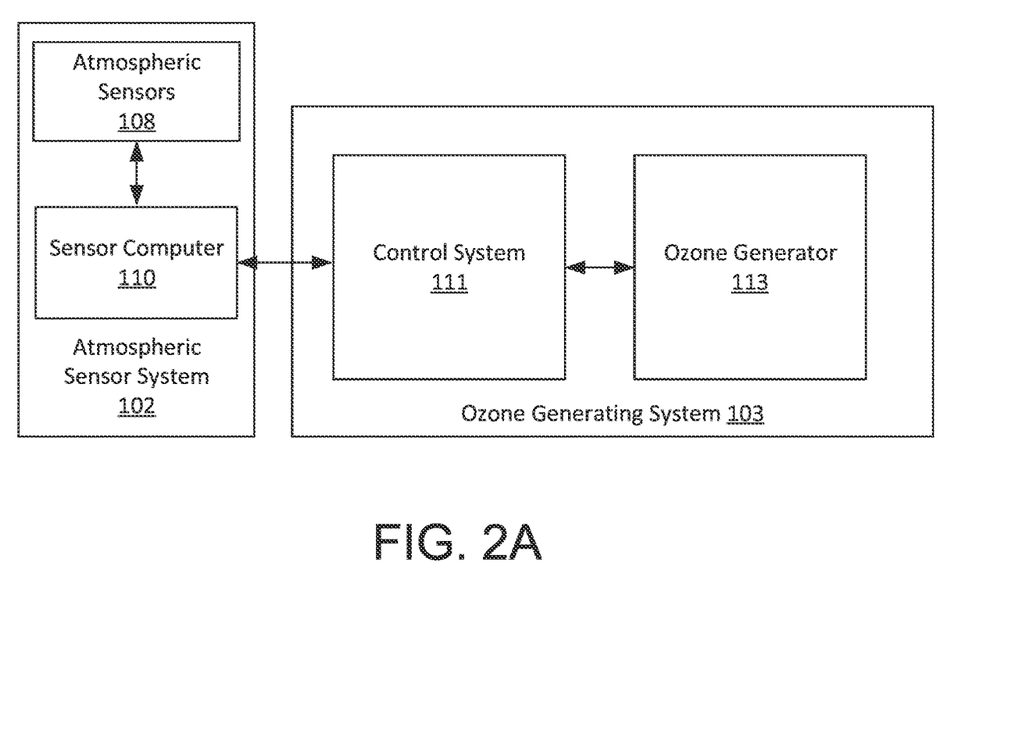
FIG. 2A is a block diagram of an example atmospheric sensor system in communication with an ozone generating system, in accordance with various embodiments of the disclosure.
Figure 2B:
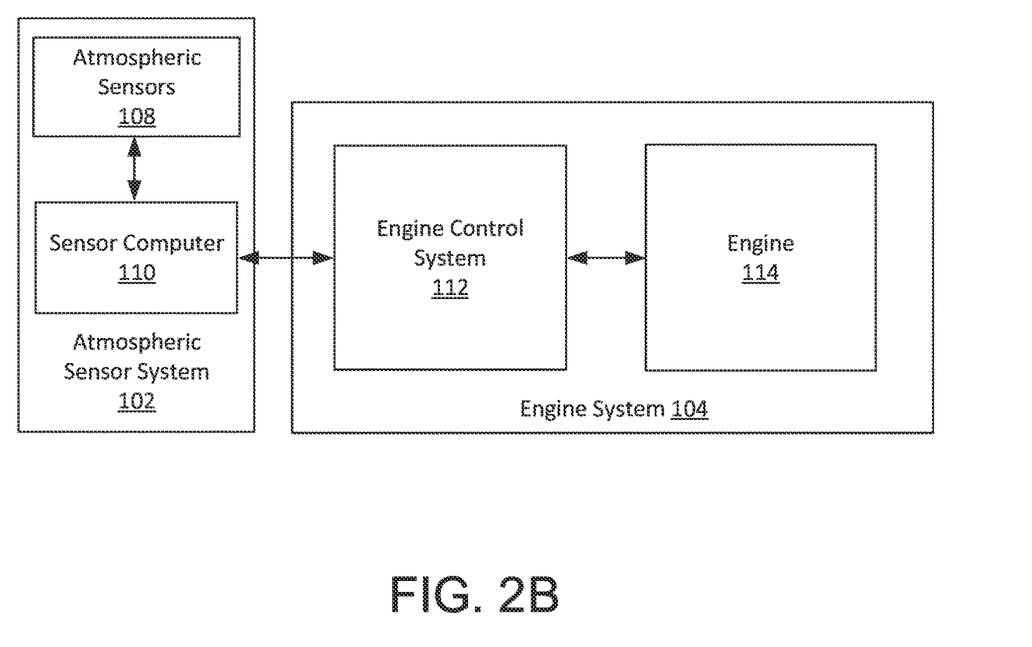
FIG. 2B is a block diagram of an example atmospheric sensor system in communication with an engine system, in accordance with various embodiments of the disclosure.
Figure 2C:
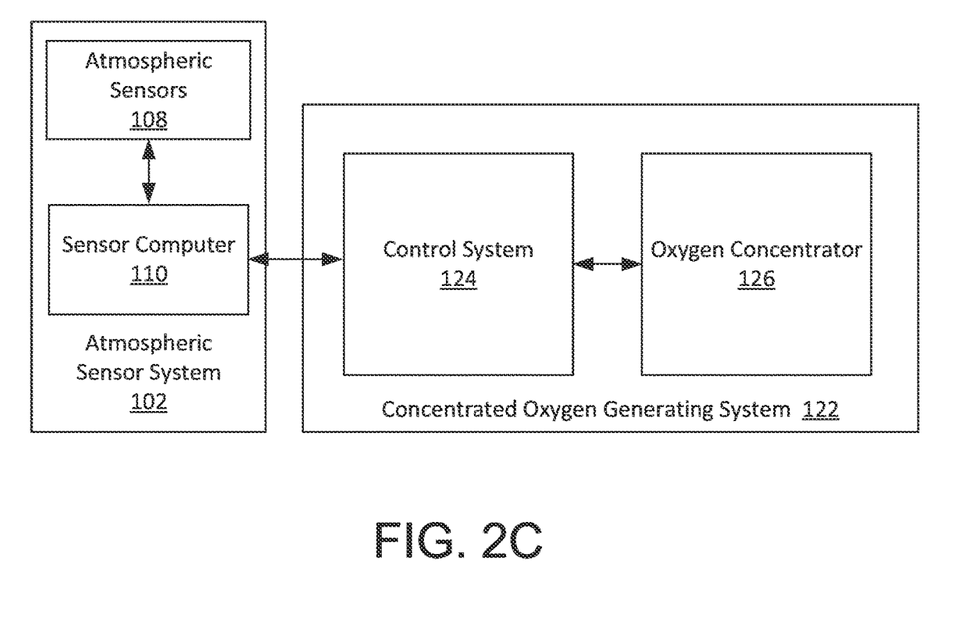
FIG. 2C is a block diagram of an example atmospheric sensor system in communication with a concentrated oxygen generating system, in accordance with various embodiments of the disclosure.

With reference to FIGS. 2A, 2B, and 2C, the atmospheric sensor system 102 may include atmospheric sensors 108 and a sensor computer 110 in communication with the atmospheric sensors. Generally, the atmospheric sensors 108 may collect various measurements from the surrounding atmosphere, which may be used by the sensor computer 110 to calculate or estimate atmospheric oxygen levels. In various examples, the atmospheric sensors 108 may communicate with the sensor computer 110 through hard-wired connections. For example, the atmospheric sensors 108 may be integrated with the sensor computer 110 through peripheral connections. The atmospheric sensors 108 may further communicate with the sensor computer 110 through various serial connections or other physical mediums used to transmit data. In some examples, the atmospheric sensors 108 may communicate with the sensor computer 110 through wireless communication protocols, such as a Bluetooth connection.

In various examples, atmospheric sensors 108 may include any number of sensors which are able to detect one or more atmospheric conditions which may be used to calculate or approximate atmospheric oxygen levels. For example, sensors which may be included in atmospheric sensors 108 may include, in various examples, altimeters, thermometers, barometric pressure sensors, humidity sensors, among others. Atmospheric sensors 108 may include one or more sensors described above. For example, in some implementations, atmospheric sensors 108 may include only an altimeter. In other examples, atmospheric sensors 108 may include an altimeter in conjunction with other sensors, such as a thermometer and a humidity sensor.

In various examples, the atmospheric sensors 108 may be in communication with a sensor computer 110 to pass data collected from the atmospheric sensors 108 to the sensor computer 110. The sensor computer 110 may utilize data collected by the atmospheric sensors 108 to determine atmospheric oxygen levels, which may be utilized to alter one or more engine inputs. For example, an altimeter of the atmospheric sensors 108 may detect an altitude of the engine, and the altitude measurement may be passed on to the sensor computer 110 determine an atmospheric oxygen level based on the altitude measurement. In other examples, multiple sensors of the atmospheric sensors 108 may pass readings and/or measurements to the sensor computer 110. For example, an altimeter, thermometer, and pressure sensor may each pass readings to the sensor computer 110 for calculation of atmospheric oxygen.

The sensor computer 110 may receive readings and/or measurements from atmospheric sensors 108 to calculate, estimate, or otherwise determine atmospheric oxygen levels. In some examples, the sensor computer 110 may receive additional data or measurements from components of the engine system 104, which may be used in addition to measurements from the atmospheric sensors 108 to determine atmospheric oxygen levels. For example, the sensor computer 110 may receive readings from an oxygen sensor measuring oxygen concentration at an outlet or exhaust of the engine 114. Such additional information may be useful for providing feedback to the sensor computer 110 and/or may be used to calibrate sensors of the atmospheric sensors 108. The sensor computer 110 may, however, be able to determine atmospheric oxygen levels without input from the engine system 104 (e.g., based on readings from atmospheric sensors 108) such that the atmospheric sensor system 102 may be used in place of conventional oxygen sensors and/or upon failure or malfunction of such oxygen sensors.

In some examples, the sensor computer 110 may receive additional information from remote locations (e.g., GPS or cloud computing locations) when available. Accordingly, the sensor computer 110 may have the ability to determine atmospheric oxygen levels based only on readings from the atmospheric sensors 108 and may be able to utilize additional information to determine atmospheric oxygen levels when available. For example, the atmospheric sensor system 102 may further integrate additional information from GPS satellites, cloud computing locations, and other sources of data accessible using, for example, a cellular data signal. The sensor computer 110 may, however, be able to determine atmospheric oxygen levels without input from such external sources, such that the atmospheric sensor system 102 may be used in locations with limited or no connectivity to GPS satellites, cellular data signals, and the like.

Figure 3:
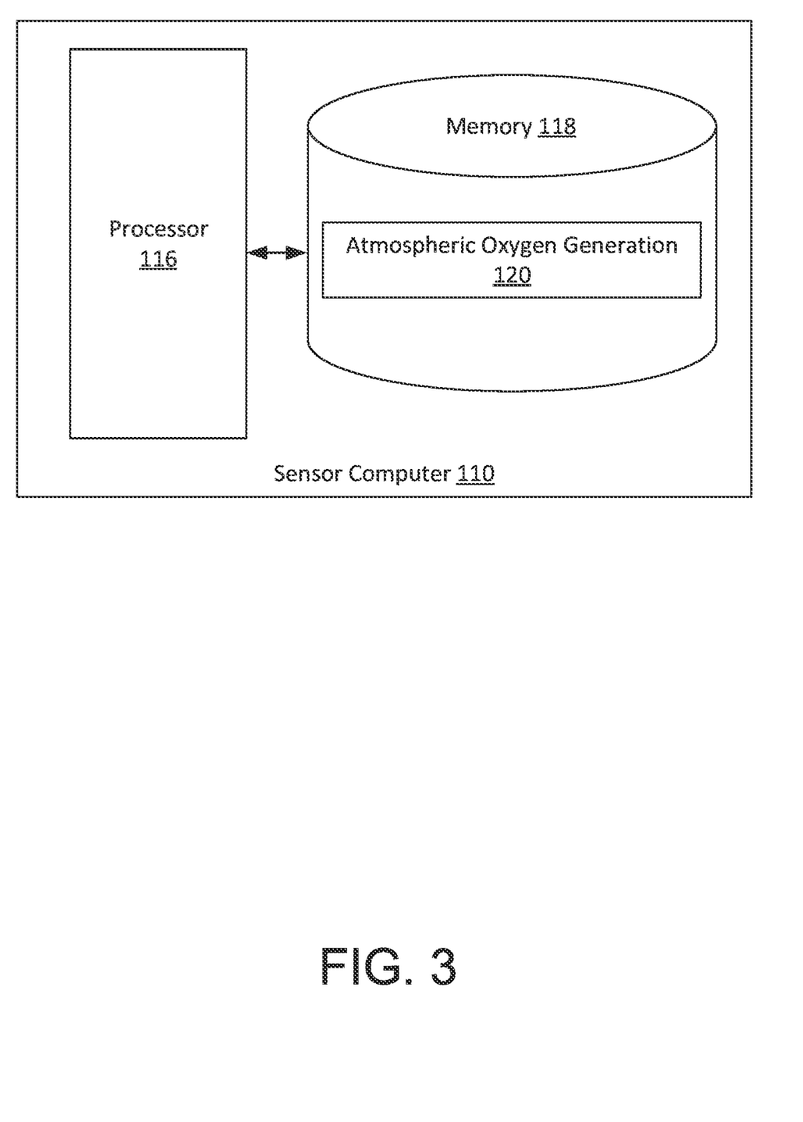
FIG. 3 is a schematic diagram of an example atmospheric sensor computer, in accordance with various embodiments of the disclosure.

With reference to FIG. 3, a sensor computer 110 may include memory 118 and one or more processors 116 which may execute instructions stored at the memory 118 of the sensor computer 110. In some examples, the memory 118 may further store additional data used by the sensor computer 110 in determining atmospheric oxygen content. For example, the memory 118 may include databases estimating oxygen content at various altitudes, constants, formulas, or other data used in calculating atmospheric oxygen content, and the like.

In some examples, the memory 118 may include instructions for atmospheric oxygen generation 120. Such instructions may, when executed by the processor 116 of the sensor computer 110, calculate an estimation of atmospheric oxygen content based on data collected by the atmospheric sensors 108 of the atmospheric sensor system 102. For example, such instructions for atmospheric oxygen generation 120 may retrieve data received at the sensor computer 110 from atmospheric sensors 108 and may format such data for use in calculations of atmospheric oxygen content. In some examples, the instructions for atmospheric oxygen generation 120 may retrieve additional data received at the sensor computer 110, such as data received from oxygen sensors of the engine, GPS data, weather data, or other data which may, in some examples, be received from sources other than the atmospheric sensors 108 of the atmospheric sensor system 102.

The instructions for atmospheric oxygen generation 120 may further select a method for calculating atmospheric oxygen estimations based on what type of data and/or measurements are received at the sensor computer 110. For example, the instructions for atmospheric oxygen generation 120 may use a different formula to calculate or estimate atmospheric oxygen content when the sensor computer 110 receives data from an altitude sensor of the atmospheric sensors 108 than when the sensor computer 110 receives data from each of an altitude sensor, a thermometer, and a pressure sensor of the atmospheric sensors 102. Further, the instructions for atmospheric oxygen generation 120 may use different methods when the sensor computer 110 receives data from sources other than the atmospheric sensors 108, such as from an oxygen sensor of the engine or from a remote location, such as GPS data, than when the sensor computer 110 uses only data from the atmospheric sensors 108. For example, atmospheric oxygen generation 120 may, when data from the atmospheric sensors 108 conflicts with data received from an external source, atmospheric oxygen generation 120 may rely on data received from the atmospheric sensors 108 over data received from external sources.

In some examples, the instructions for atmospheric oxygen generation 120 may calculate or determine atmospheric oxygen content responsive to changes in data received from the atmospheric oxygen sensors 108. For example, upon receiving measurements from an altimeter of the atmospheric oxygen sensors 108 showing a change in altitude, the instructions for atmospheric oxygen generation 120 may calculate the atmospheric oxygen content based on the changed altitude. In contrast, where the altitude (or other measured values) are unchanged, the instructions for atmospheric oxygen generation 120 may not continuously calculate atmospheric oxygen content. In this manner, the atmospheric sensor system 102 may be responsive to changes in the atmosphere, such as vehicles traveling over terrain with changing elevation and altitude or landscaping or construction equipment used over a time period with changing temperatures, while not expending excess energy where conditions are not changing, such as for an engine used in a stationary generator.

Instructions for atmospheric oxygen generation 120 may further, in some examples, calibrate various sensors of the atmospheric sensors 108. For example, where the sensor computer 110 receives external data, the instructions for atmospheric oxygen generation 120 may compare values from the atmospheric oxygen sensors 108 to expected values to detect malfunction or need for calibration of the atmospheric oxygen sensors 108. For example, the sensor computer 110 may receive data from a GPS system indicating that the expected altitude is 3000 feet. Where the data from an altitude sensor of the atmospheric oxygen sensors 108 measures altitude at 8000 feet at the same time, the instructions for atmospheric oxygen generation 120 may determine that the altitude sensor has failed. In such examples, the sensor computer 110 may rely on other sensors of the atmospheric oxygen sensors 108 for calculation of atmospheric oxygen content and may further generate warnings or indicators to check or repair the altitude sensor, such as by illuminating a warning light or relaying a warning to a mobile device in communication with the atmospheric sensor system 102.

With reference to FIG. 2A, the atmospheric sensor system 102 may be in communication with an ozone generating system 103. The ozone generating system 103 may be, in various examples, an ultraviolet (UV) ozone generator, a corona discharge ozone generator, or other type of ozone generator using atmospheric oxygen to create ozone. The ozone generating system 103 may include a control system 111 and an ozone generator 113. In various examples, the control system 111 may control mechanical or electrical operation of one or more components of the ozone generator 113. The ozone generator 113 may generally intake ambient or atmospheric air and use atmospheric oxygen from the ambient air to generate ozone.

In some examples, the control system 111 may control operation of the intake mechanism for ambient air at the ozone generator 113. Accordingly, the control system 111 may adjust the intake mechanism to intake more or less ambient air depending, for example, on the atmospheric oxygen content received from the sensor computer 110. For example, to keep ozone generation consistent, the control system 111 may adjust a speed of a fan used to intake ambient air into the ozone generator 113 to intake a higher volume of ambient air when the atmospheric oxygen content provided by the sensor computer 110 shows lower levels of atmospheric oxygen. In these examples, the control system 111 may adjust the air intake mechanism to keep the amount of oxygen available for the production of ozone more consistent, even where the amount of oxygen in the ambient air changes.

With reference to FIG. 2B, the atmospheric sensor system 102 may be in communication with an engine system 104. In various examples, the engine system 104 may include an engine control system 112 and an engine 114. The engine control system 112 may generally receive atmospheric oxygen content from the sensor computer 110 of the atmospheric sensor system 102 and may adjust operations of the engine 114 to compensate for changes in atmospheric oxygen content. For example, the engine control system 112 may determine an amount of fuel to inject into the engine 114 based on the atmospheric oxygen content provided by the sensor computer 110. The engine control system 112 may then actuate fuel injection valves or provide signals to other actuators of the engine controlling fuel injection to adjust the fuel to oxygen ratio of the engine 114. The engine control system 112 may receive readings from additional sensors of the engine monitoring characteristics such as manifold absolute pressure, intake air temperature, crank shaft position, throttle position, acceleration pedal position, and the like.

In some examples, the engine control system 112 may further control systems dealing with engine byproducts, such as air injection systems. For example, an air injection system may decrease hydrocarbon and carbon monoxide emissions by providing air to the engine exhaust, where oxygen in such air helps burn any unburned fuel before exhaust from the engine, reducing hydrocarbon and carbon monoxide emissions. In these examples, the engine control system 112 may determine an amount of air to inject into parts of the engine exhaust based on atmospheric oxygen content provided by the sensor computer 110. For example, where atmospheric oxygen content drops, the engine control system 112 may actuate air pumps, air valves, or other components of the engine 114 to provide additional air to exhaust ports of the engine, keeping the amount of oxygen provided to the exhaust ports more consistent.

The engine control system 112 may include various electronic components monitoring performance of the engine 114 and/or controlling engine operation characteristics of the engine. For example, the engine control system 112 may adjust valves of the engine 114 controlling fuel injection to maintain a proper fuel to oxygen ratio within the engine 114. The engine control system 112 may also adjust various components of an air injection system to maintain a proper level of oxygen to reduce emissions of byproducts from the engine 114. The engine control system 112 may, in various examples, be an engine control system 112 provided with the engine 114, such as an engine control unit (ECU), engine control module (ECM), or the like, adjusting various actuators of the engine 114 and/or systems of the engine to adjust engine performance. In various examples, the engine control system 112 may further include processors and memory with instructions which, when executed by the processors, determine how to adjust engine inputs and/or operations based on atmospheric oxygen levels. The memory may further include data, such as look up tables and the like, to assist the engine control system 112 in making such determinations.

The engine 114 may be a gas powered, diesel powered, or other engine controlled by the engine control system 112. In various examples, the engine may include components in communication with the engine control system 112 and actuated by the engine control system 112 to adjust engine performance, such as fuel injection valves, throttle stops, stepper motors, air pumps, nozzles, and the like.

With reference to FIG. 2C, the atmospheric sensor system 102 may be in communication with a concentrated oxygen generating system 122. In various examples, the concentrated oxygen generating system 122 may include a control system 124 and an oxygen concentrator 126. The oxygen concentrator 126 may be, in various examples, a system for creating liquid oxygen from ambient air, concentrated oxygen from ambient air, and the like. In various examples, the control system 124 may control mechanical or electrical operation of one or more components of the oxygen concentrator 126. The oxygen concentrator 126 may generally intake ambient or atmospheric air and use atmospheric oxygen from ambient air to generate concentrated or liquid oxygen.

In various examples, the control system 124 may control operation of an intake mechanism for ambient air at the oxygen concentrator 126. Accordingly, the control system 124 may adjust the intake mechanism to intake more or less air depending, for example, on the atmospheric oxygen content received from the sensor computer 110. For example, to generate a consistent or higher amount of concentrated or liquid oxygen, the control system may adjust a speed of a fan used to intake ambient air into the oxygen generator 126 to intake a higher volume of ambient air when the atmospheric oxygen content provided by the sensor computer 110 shows lower levels of atmospheric oxygen. In these examples, the control system 124 may adjust the air intake mechanism to keep the amount of oxygen available for the production of concentrated or liquid oxygen more consistent, even where the amount of oxygen in the ambient air changes.

Figure 2D:
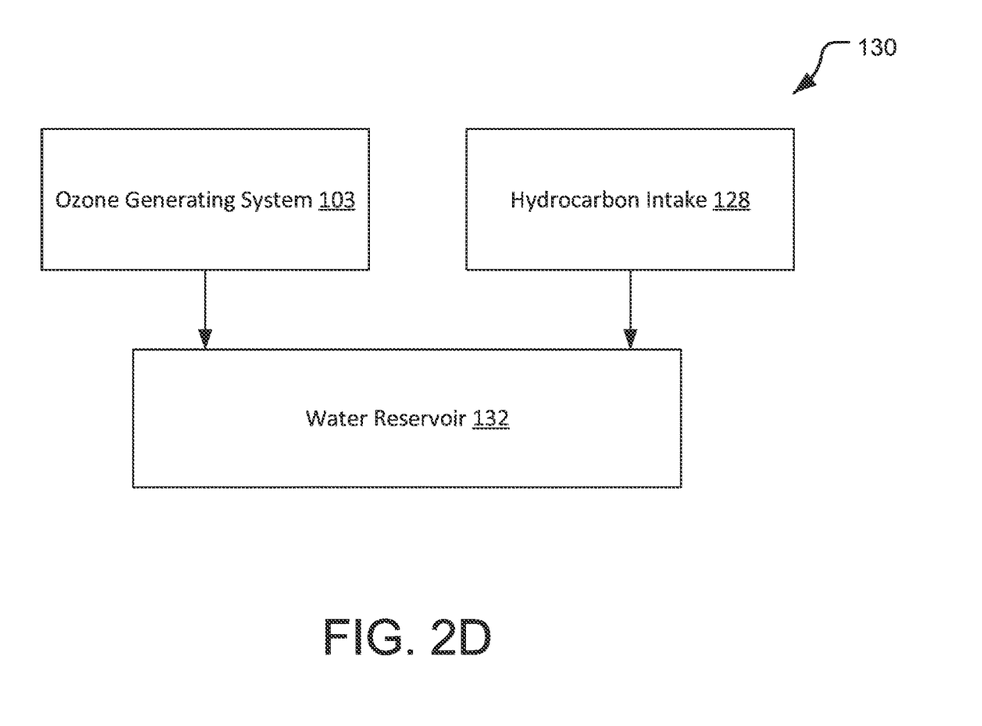
FIG. 2D is a block diagram of an example system for generation of water using ozone and hydrocarbons, in accordance with various embodiments of the disclosure.

With reference to FIG. 2D, an example system 130 may be used for generation of water using ozone and hydrocarbons. The system 130 may be used with or without the atmospheric oxygen sensor system 102, in various examples. For example, the atmospheric oxygen sensor system 102 may control or be in communication with the ozone generating system 103. The ozone generator 103 may generally intake ambient or atmospheric air and use the atmospheric oxygen from the ambient air to generate ozone, as described herein. Hydrocarbon intake 128 may generally obtain hydrocarbons from various sources including, for example, hydrocarbons generated as byproduct of fuel burning. The ozone generated by the ozone generating system 103 may then be combined with (e.g., chemically react with) hydrocarbons brought into the system by hydrocarbon intake 128 to generate water as a byproduct which may be stored in, for example, a water reservoir 132. In some examples, water within the water reservoir 132 may be further treated with additional ozone created by the ozone generating system 103 to create a usable water source while removing hydrocarbons from the environment.

Figure 2E:
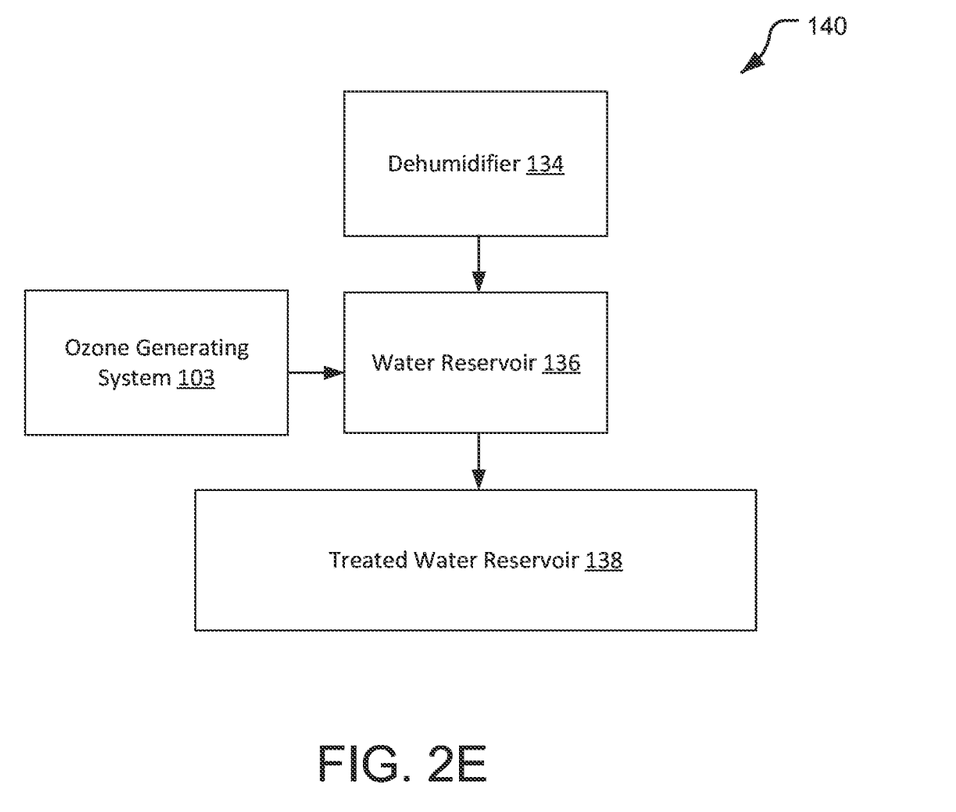
FIG. 2E is a block diagram of an example system for treatment of water using ozone, in accordance with various embodiments of the disclosure.

With reference to FIG. 2E, an example system 140 may be used for treatment of water using ozone. The system 140 may be used with or without the atmospheric oxygen sensor system 102, in various examples. For example, the atmospheric oxygen sensor system 102 may control or be in communication with the ozone generating system 103 and/or the dehumidifier 134, in various examples. The ozone generator 103 may generally intake ambient or atmospheric air and use the atmospheric oxygen from the ambient air to generate ozone, as described herein. A dehumidifier 134 may intake atmospheric air to remove moisture from the atmospheric air. The dehumidifier 134 may return dehumidified air to the environment. Water may be created as a byproduct of the dehumidification, which may be stored, for example, in a water reservoir 136. Ozone created by the ozone generating system 103 may be used to treat water, such as wastewater or water with impurities or contaminants, in the water reservoir 136 to create clean water sources for, for example, drinking water. Such clean water may be, in some examples, stored in a treated water reservoir 138.

Figure 4:
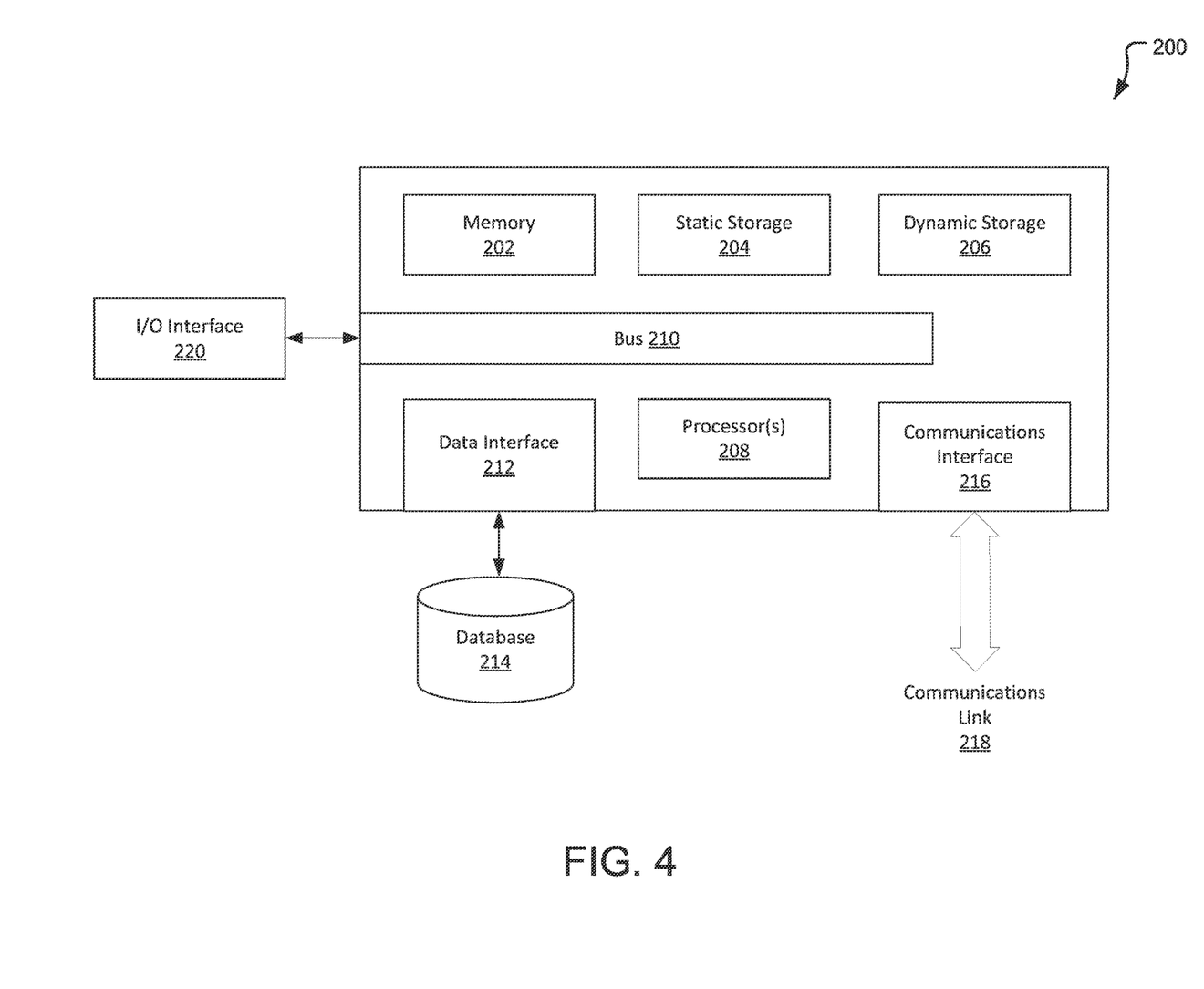
FIG. 4 is a schematic diagram of a computer system which may be used to implement various embodiments in the examples described herein.

FIG. 4 is a schematic diagram of a computing system 200 which may be used to implement various embodiments in the examples described herein. For example, processor 116 and memory 118 may be located at one or several computing systems 200. In various embodiments, one or more components of the atmospheric sensor system 102 and/or the engine system 104 may be also implemented by a computing system 200. For example, the sensor computer 110 and/or the engine control system 112 may be implemented by a computing system 200. This disclosure contemplates any suitable number of computing systems 200. For example, a computing system 200 may be a server, a desktop computing system, a mainframe, a mesh of computing systems, a laptop or notebook computing system, a tablet computing system, or a combination of two or more of these. Where appropriate, the computing system 200 may include one or more computing systems; be unitary or distributed; span multiple locations; span multiple machines; span multiple data centers; or reside in a cloud, which may include one or more cloud components in one or more networks.

Computing system 200 includes a bus 210 (e.g., an address bus and a data bus) or other communication mechanism for communicating information, which interconnects subsystems and devices, such as processor 208, memory 202 (e.g., RAM), static storage 204 (e.g., ROM), dynamic storage 206 (e.g., magnetic or optical), communications interface 216 (e.g., modem, Ethernet card, a network interface controller (NIC) or network adapter for communicating with an Ethernet or other wire-based network, a wireless NIC (WNIC) or wireless adapter for communicating with a wireless network, such as a WI-FI network), input/output (I/O) interface 220 (e.g., a keyboard, keypad, mouse, microphone). In particular embodiments, the computing system 200 may include one or more of any such components.

In particular embodiments, processor 208 includes hardware for executing instructions, such as those making up a computer program. The processor 208 circuity includes circuitry for performing various processing functions, such as executing specific software for perform specific calculations or tasks. In particular embodiments, I/O interface 220 includes hardware, software, or both, providing one or more interfaces for communication between computing system 200 and one or more I/O devices. Computing system 200 may include one or more of these I/O devices, where appropriate. One or more of these I/O devices may enable communication between a person and computing system 200.

In particular embodiments, communications interface 216 includes hardware, software, or both providing one or more interfaces for communication (such as, for example, packet-based communication) between computing system 200 and one or more other computer systems or one or more networks. One or more memory buses (which may each include an address bus and a data bus) may couple processor 208 to memory 202. Bus 210 may include one or more memory buses, as described below. In particular embodiments, one or more memory management units (MMUs) reside between processor 208 and memory 202 and facilitate accesses to memory 202 requested by processor 208. In particular embodiments, bus 210 includes hardware, software, or both coupling components of computing system 200 to each other.

According to particular embodiments, computing system 200 performs specific operations by processor 208 executing one or more sequences of one or more instructions contained in memory 202. For example, instructions for application rate protocol generation 122 may be contained in memory 202 and may be executed by the processor 208. Such instructions may be read into memory 202 from another computer readable/usable medium, such as static storage 204 or dynamic storage 206. In alternative embodiments, hard-wired circuitry may be used in place of or in combination with software instructions. Thus, particular embodiments are not limited to any specific combination of hardware circuitry and/or software. In one embodiment, the term "logic" shall mean any combination of software or hardware that is used to implement all or part of particular embodiments disclosed herein.

The term "computer readable medium" or "computer usable medium" as used herein refers to any medium that participates in providing instructions to processor 208 for execution. Such a medium may take many forms, including but not limited to, nonvolatile media and volatile media. Non-volatile media includes, for example, optical or magnetic disks, such as static storage 204 or dynamic storage 206. Volatile media includes dynamic memory, such as memory 202.

Computing system 200 may transmit and receive messages, data, and instructions, including program, e.g., application code, through communications link 218 and communications interface 216. Received program code may be executed by processor 208 as it is received, and/or stored in static storage 204 or dynamic storage 206, or other storage for later execution. A database 214 may be used to store data accessible by the computing system 200 by way of data interface 212.

Figure 5:
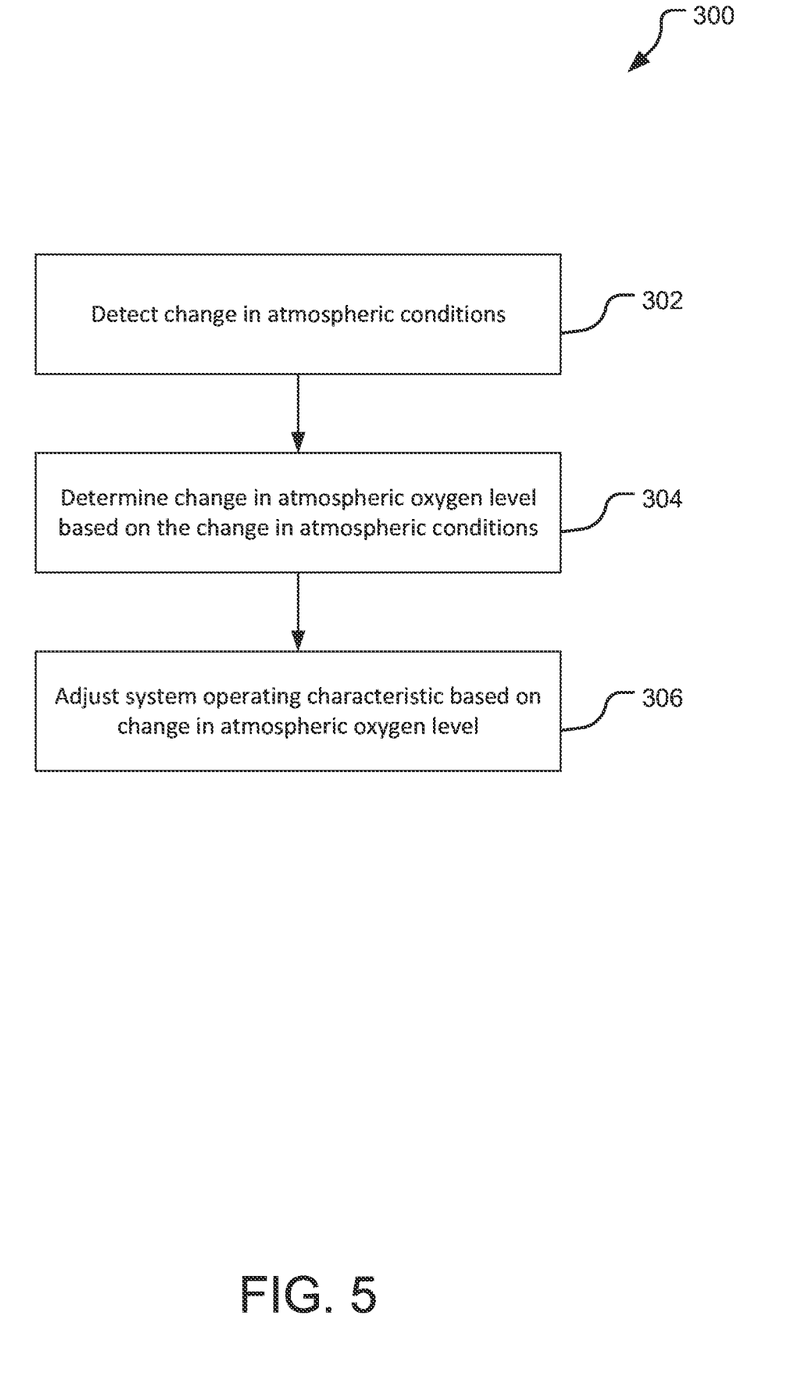
FIG. 5 is a flow diagram of an example process for adjusting engine inputs based on atmospheric oxygen levels in accordance with various embodiments of the disclosure.

FIG. 5 is a flow diagram of an example process 300 for adjusting engine inputs based on atmospheric oxygen levels. In some examples, the process 300 may be continual, such that the atmospheric sensors 108 continually measure atmospheric conditions and the sensor computer 110 continually updates atmospheric oxygen content based on readings from the atmospheric sensors 108. In other examples, the process 300 may be triggered by some event, such as a command received from a mobile device in communication with the atmospheric sensor system 102, actuation of an element of the atmospheric sensor system 102 by a user (e.g., a button, switch, or the like), or other event.

At block 302, the atmospheric sensor system 102 may detect a change in atmospheric conditions. Atmospheric conditions, such as altitude, temperature, pressure, and the like, may be detected by the atmospheric sensors 108 of the atmospheric sensor system 102. In various examples, the sensor computer 110 may compare the conditions detected by the atmospheric sensors 108 to previously received values to detect a change in the values. In such examples, the sensor computer 110 may proceed to block 304 to determine the atmospheric oxygen level only when there is a significant change in the values detected by the atmospheric sensors 108. For example, a significant change may be one where the value changes more than a threshold percentage (e.g., more than a 5% value change either way). After detecting the change in atmospheric conditions, the atmospheric sensors 108 may communicate or pass along readings to the sensor computer 110 of the atmospheric sensor system 102.

The atmospheric sensor system 102 may determine a change in the atmospheric oxygen level based on the change in atmospheric conditions at block 304. After receiving readings or measurements from the atmospheric sensors 108, the sensor computer 110 may calculate or determine atmospheric oxygen content based on such readings or measurements. In some examples, the sensor computer 110 may utilize different formulas or methods for determining atmospheric oxygen content depending on what types of data the sensor computer 110 receives from the atmospheric sensors 108. For example, a different formula may be used when the sensor computer 110 receives data only from an altitude sensor of the atmospheric sensors 108 and when the sensor computer 110 receives data from an altitude sensor, thermometer, and a pressure sensor of the atmospheric sensors 108.

In some examples, the atmospheric sensor system 102 may further determine a change in the atmospheric oxygen level (e.g., the atmospheric oxygen content) based on data received from other sources, such as GPS data, weather data or other data received from cloud computing locations, and/or data received from other sensors used by the engine 114 or ozone generator 113.

In some examples, the atmospheric sensor system 102 (e.g., the sensor computer 110) may communicate atmospheric readings and/or changes in atmospheric oxygen levels to one or more devices in communication with the atmospheric sensor system 102. For example, the sensor computer 110 may provide a change in altitude to a mobile device in communication with the atmospheric sensor system 102, and the new altitude may be provided to the user via a user interface of the mobile device, such as via a notification or within a mobile application. In another example, the sensor computer 110 may provide the updated atmospheric oxygen level to a passenger in a vehicle through, for example, an infotainment system on the interior of the vehicle.

At block 306, system operating characteristics may be adjusted based on the change in the atmospheric oxygen level. System operating characteristics may include inputs to an engine 114, inputs to systems controlling byproducts of an engine 114 (e.g., an air injection system), ambient air input to an ozone generator 113, and the like.

For example, when adjusting engine inputs, after determining the change in atmospheric oxygen content, the sensor computer 110 may transmit the updated atmospheric oxygen content to the engine system 104, such as to the engine control system 112. The engine control system 112 may then determine how to adjust engine inputs based on the updated atmospheric oxygen content. For example, where the atmospheric oxygen content has significantly increased, the engine control system 112 may determine that more fuel should be injected into the engine 114 in order to maintain the fuel to oxygen ratio of the engine. The engine control system 112 may then actuate one or more inputs of the engine to make such adjustments. For example, the engine control system 112 may actuate one or more valves controlling fuel injectors for the engine 114.

In another example, when adjusting inputs to a system controlling byproducts of an engine (e.g., an air injection system), the sensor computer 110 may transmit the updated atmospheric oxygen content to the engine system 104, such as to the engine control system 112. The engine control system 112 may then determine how to adjust inputs to the air injection system based on the updated atmospheric oxygen content. For example, the engine control system 112 may actuate an air pump and/or one or more nozzles or valves controlling air flow to make such adjustments. The adjustments may generally cause the air injection system to provide enough oxygen to effectively reduce hydrocarbon, carbon monoxide, or other undesirable emissions from the engine 114.

In another example, when adjusting inputs to an ozone generator or other oxidant output source, the sensor computer 110 may transmit the updated oxygen atmospheric oxygen content to the ozone generating system 103, such as to the control system 111. The control system 111 may then determine how to adjust operating characteristics of the ozone generator 113 to maintain ozone production. For example, where the atmospheric oxygen content has decreased, the control system 111 may actuate a fan or other air intake device of the ozone generator 113 to intake more ambient air (e.g., enough to keep the incoming oxygen content stable).

Using the system and methods described above, an atmospheric sensor system 102 may be used to maintain engine performance in various settings, including locations where external data, such as GPS data or data received over a cellular network, is not available. The atmospheric sensor system 102 may further provide redundancy for systems using oxygen sensors, such that engine performance may be maintained in the event of oxygen sensor failure or malfunction.

The technology described herein may be implemented as logical operations and/or modules in one or more systems. The logical operations may be implemented as a sequence of processor-implemented steps directed by software programs executing in one or more computer systems and as interconnected machine or circuit modules within one or more computer systems, or as a combination of both. Likewise, the descriptions of various component modules may be provided in terms of operations executed or effected by the modules. The resulting implementation is a matter of choice, dependent on the performance requirements of the underlying system implementing the described technology. Accordingly, the logical operations making up the embodiments of the technology described herein are referred to variously as operations, steps, objects, or modules. Furthermore, it should be understood that logical operations may be performed in any order, unless explicitly claimed otherwise or a specific order is inherently necessitated by the claim language.

In some implementations, articles of manufacture are provided as computer program products that cause the instantiation of operations on a computer system to implement the procedural operations. One implementation of a computer program product provides a non-transitory computer program storage medium readable by a computer system and encoding a computer program. It should further be understood that the described technology may be employed in special purpose devices independent of a personal computer.

The above specification, examples and data provide a complete description of the structure and use of exemplary embodiments of the invention as defined in the claims. Although various embodiments of the claimed invention have been described above with a certain degree of particularity, or with reference to one or more individual embodiments, it is appreciated that numerous alterations to the disclosed embodiments without departing from the spirit or scope of the claimed invention may be possible. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A method of adjusting one or more operating characteristics of an oxygen utilizing system based on atmospheric oxygen content, the method comprising:
   detecting, using one or more atmospheric sensors that exclude an oxygen sensor, atmospheric conditions for an atmosphere surrounding the oxygen utilizing system;
   determining, without using oxygen sensor input, the atmospheric oxygen content based on the detected atmospheric conditions; and
   adjusting the one or more operating characteristics of the oxygen utilizing system based on the atmospheric oxygen content, wherein the oxygen utilizing system includes one of:
      an ozone generator, and adjusting the one or more operating characteristics comprises actuating a first air intake device to adjust how much ambient air is provided to the ozone generator;
      an engine, and adjusting the one or more operating characteristics for the engine comprises actuating one or more motor components, valves, pumps, nozzles, or throttle stops to control fuel injection or air injection to the engine; or
      an oxygen concentrator, and adjusting the one or more operating characteristics for the oxygen concentrator comprises actuating a second air intake device to adjust how much ambient air is provided to the oxygen concentrator.

2. The method of claim 1, wherein the one or more atmospheric sensors is mounted to an exterior surface of a vehicle implemented with the oxygen utilizing system.

3. The method of claim 1, wherein the one or more atmospheric sensors include one or more of an altimeter, a thermometer, and a pressure sensor.

4. The method of claim 1, wherein the atmospheric oxygen content is further based on data from one or more global positioning system (GPS) satellites.

5. The method of claim 1, wherein the first air intake device is configured to vary intake of the ambient air such that generation of ozone output is consistent.

6. The method of claim 1, wherein the one or more atmospheric sensors comprises a global positioning system (GPS) sensor.

7. A system, comprising:
one or more atmospheric sensors configured to detect atmospheric conditions of an atmosphere surrounding an oxygen utilizing system, the atmospheric conditions comprising at least one of altitude, atmospheric temperature, or atmospheric air pressure;
a sensor computer in communication with the one or more atmospheric sensors, the sensor computer being configured to determine an atmospheric oxygen content without input from an oxygen sensor, the atmospheric oxygen content based on the detected atmospheric conditions received from the one or more atmospheric sensors; and
a control system for the oxygen utilizing system, the oxygen utilizing system being in communication with the sensor computer, and the control system being configured to adjust one or more operating characteristics of the oxygen utilizing system based on the atmospheric oxygen content received from the sensor computer, wherein the oxygen utilizing system includes one of:
an ozone generator, and adjusting the one or more operating characteristics comprises actuating a first air intake device to adjust how much ambient air is provided to the ozone generator;
an engine, and adjusting the one or more operating characteristics for the engine comprises actuating one or more motor components, valves, pumps, nozzles, or throttle stops to control fuel injection or air injection to the engine; or
an oxygen concentrator, and adjusting the one or more operating characteristics for the oxygen concentrator comprises actuating a second air intake device to adjust how much ambient air is provided to the oxygen concentrator.

8. The system of claim 7, wherein the first air intake device is configured to vary intake of the ambient air such that generation of ozone output is consistent.

9. The system of claim 7, wherein adjusting the one or more operating characteristics of the oxygen utilizing system occurs in response to detected changes of the atmospheric conditions.

10. The system of claim 7, wherein the one or more atmospheric sensors are externally mounted to a vehicle.

11. The system of claim 10, wherein the one or more atmospheric sensors include one or more of an altimeter, a thermometer, and a pressure sensor.

12. The system of claim 7, further comprising a hyrdrocarbone intake configured to intake hydrocarbons, wherein ozone output of the ozone generator is combinable with the hydrocarbons to generate water.

13. The system of claim 7, further comprising a dehumidifier configured to generate water output, wherein the ozone output of the ozone generator is combinable with the water output to treat the water output.

14. One or more non-transitory computer readable media encoded with instructions which, when executed by one or more processors, cause the one or more processors to:
receive, from one or more atmospheric sensors, atmospheric conditions for an atmosphere surrounding an oxygen utilizing system, wherein the one or more atmospheric sensors do not include sensors directly measuring oxygen content;
determine, without a measured oxygen value, an atmospheric oxygen content based on the received atmospheric conditions; and
adjust one or more operating characteristics of the oxygen utilizing system based on the atmospheric oxygen content to generate a consistent output of the oxygen utilizing system, wherein the oxygen utilizing system includes one of:
an ozone generator, and adjusting the one or more operating characteristics comprises actuating a first air intake device to adjust how much ambient air is provided to the ozone generator;
an engine, and adjusting the one or more operating characteristics for the engine comprises actuating one or more motor components, valves, pumps, nozzles, or throttle stops to control fuel injection or air injection to the engine; or
an oxygen concentrator, and adjusting the one or more operating characteristics for the oxygen concentrator comprises actuating a second air intake device to adjust how much ambient air is provided to the oxygen concentrator.

15. The computer readable media of claim 14, wherein the instructions further cause the one or more processors to determine the atmospheric oxygen content based on data from one or more global positioning system (GPS) satellites.

16. The computer readable media of claim 15, wherein the one or more atmospheric sensors include one or more of sensors measuring altitude, temperature, and pressure of the atmosphere surrounding the oxygen utilizing system.

17. The computer readable media of claim 14, wherein the instructions further cause the one or more processors to adjust the one or more operating characteristics of the oxygen utilizing system occurs in response to detected changes of the atmospheric conditions.

* * * * *